United States Patent
Bowman et al.

(10) Patent No.: US 8,674,149 B2
(45) Date of Patent: Mar. 18, 2014

(54) OXIDATIVE MONO-HALOGENATION OF METHANE

(75) Inventors: Robert G. Bowman, Woodbury, MN (US); Eric E. Stangland, Midland, MI (US); Mark E. Jones, Midland, MI (US); Dean M. Millar, Midland, MI (US); Simon G. Podkolzin, Midland, MI (US); Brien A. Stears, League City, TX (US); Richard M. Wehmeyer, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 503 days.

(21) Appl. No.: 13/123,908

(22) PCT Filed: Aug. 19, 2009

(86) PCT No.: PCT/US2009/054314
§ 371 (c)(1),
(2), (4) Date: Apr. 13, 2011

(87) PCT Pub. No.: WO2010/062427
PCT Pub. Date: Jun. 3, 2010

(65) Prior Publication Data
US 2011/0201841 A1    Aug. 18, 2011

Related U.S. Application Data

(60) Provisional application No. 61/108,616, filed on Oct. 27, 2008.

(51) Int. Cl.
*C07C 17/154*    (2006.01)
*C07C 19/03*     (2006.01)

(52) U.S. Cl.
USPC ........................................ 570/243

(58) Field of Classification Search
None
See application file for complete search history.

(56) References Cited

U.S. PATENT DOCUMENTS

| | | |
|---|---|---|
| 1,086,381 A | 2/1914 | Masland |
| 4,523,040 A | 6/1985 | Olah |
| 4,769,504 A | 9/1988 | Noceti et al. |
| 4,795,843 A | 1/1989 | Imai et al. |
| 4,990,696 A | 2/1991 | Stauffer |
| 5,354,916 A | 10/1994 | Horvath et al. |
| 5,397,560 A | 3/1995 | Millar et al. |
| 5,969,195 A | 10/1999 | Stabel et al. |
| 6,452,058 B1 | 9/2002 | Schweizer et al. |
| 2006/0167314 A1 | 7/2006 | Periana |
| 2007/0078280 A1 | 4/2007 | Bell et al. |

FOREIGN PATENT DOCUMENTS

| | | |
|---|---|---|
| WO | WO-02094749 A1 | 11/2002 |
| WO | WO-02094751 A2 | 11/2002 |
| WO | WO-03/057318 A1 | 7/2003 |
| WO | WO-2006118935 A2 | 11/2006 |
| WO | WO-2009031719 A1 | 3/2009 |

OTHER PUBLICATIONS

Batamack, Patrice, Imre Bucsi, Arpad Molnar, and George A. Olah. "Electrophilic chlorination of methane over superacidic sulfated zirconia." *Catalysis Letters.* 25. (1994): 11-19.
Fells, Ian. "The Kinetics of the Hydrolysis of the Chlorinated Methanes." *Fuel Society Jouranl.* 10. (1959): 26-35.
Manoilova, Olga V., et al "Surface Acidity and Basicity of $La_2O_3$, LaOCl, and $LaCl_3$ Characterized by IR Spectroscopy, TPD, and DFT Calculations." *Journal of Physical Chemistry B.* 108(40). (2004): 15770-781.
Matsuhashi, Hiromi, Masakazu Oikawa, and Kazushi Arata. "Formation of Superbase Sites on Alkaline Earth Metal Oxides by Doping of Alkali Metals." *Langmuir.* 16. (2000): 8201-05.
Olah, George, et al. "Selective Monohalogenation of Methane over Supported Acid or Platinum Metal Catalysts and Hydrolysis of Methyl Halides over y-Alumina-Supported Metal Oxide/Hydroxide Catalysts. A Feasible Path for the Oxidative Conversion of Methane into Methyl alcohol/Dimethyl Ether." *J. Am. Chem. Soc.* 107. (1985): 7097-7105.
Podkolzin, Simon G. Olga V. Manoilova, and Bert M. Weckhuysen. "Relative Activity of $La_2O_3$, $LaOCl_3$ in Reaction with CCl4 Studied with Infrared Spectroscopy and Density Functional Theory Calculations." *Journal of Physical Chemistry B.* 109.3 (2005): 11634-642.
Wang, Kuan Xin, Han Fei Xu, Wen Sheng Li, and Xiao Ping Zhou. "Acetic acid synthese from methane by non-synthesis gas process." *Journal of Molecular Catalysis A:Chemical.* 225. (2005): 65-69.
Wang, K.X., H.F. Xu, W.S. Li, C.T. Au, and X.P. Zhou. "The synthesis of acetic acid from methane via oxidative bromination, carbonylation, and hyddrolysis." *Applied Catalysis A: General.* 304. (2006): 168-77.
PCT/US2009/054314 International Search Report.
PCT/US2009/054314 Written Opinion.
PCT/US2009/054314 International Preliminary Report on Patentability.

*Primary Examiner* — Yevegeny Valenrod

(57) ABSTRACT

Oxidatively halogenate methane by placing a feedstream that comprises methane, a source of halogen, a source of oxygen and, optionally, a source of diluent gas in contact with a first catalyst (e.g. a solid super acid or a solid super base) that has greater selectivity to methyl halide and carbon monoxide than to methylene halide, trihalomethane or carbon tetrahalide. Improve overall selectivity to methyl halide by using a second catalyst that converts at least part of the feedstream to a mixture of methyl halide, methylene halide, trihalomethane, carbon tetrahalide and unreacted oxygen, and placing that mixture in contact with the first catalyst which converts at least a portion of the methylene halide, trihalomethane and carbon tetrahalide to carbon monoxide, hydrogen halide and water.

9 Claims, No Drawings

OXIDATIVE MONO-HALOGENATION OF METHANE

This application is a non-provisional application claiming priority from the U.S. Provisional Patent Application No. 61/108,616, filed on Oct. 27, 2008, entitled "OXIDATIVE MONO-HALOGENATION OF METHANE," the teachings of which are incorporated by reference herein, as if reproduced in full hereinbelow.

This invention generally relates to a process for oxidatively halogenating (e.g. chlorinating, brominating, iodating or fluorinating) methane to form a methyl halide (e.g. methyl chloride) and catalysts used to promote oxidative halogenation of methane. This invention particularly relates to such a process wherein methane, a source of halogen and a source of oxygen operatively contact a catalyst that has a greater selectivity to methyl halide and carbon monoxide than to methylene halide, trihalomethane or carbon tetrahalide.

Oxidative halogenation represents one route to convert methane ($CH_4$) to halogenated methane, preferably monohalogenated methane ($CH_3X$, where X represents a halogen) and more preferably monochlorinated methane ($CH_3Cl$). Monohalogenated methanes, such as methyl chloride ($CH_3Cl$), find utility in producing silicones or as intermediates in producing a variety of commodity chemicals such as methanol, dimethyl ether, light olefins (e.g. ethylene, propylene, butene and higher hydrocarbons, including gasolines that have more than five carbon atoms ($C_5^+$)), gasoline, vinyl chloride and acetic acid. While halogenated methanes that have multiple (two, three or four) halogen atoms (e.g. methylene chloride) also have some utility, a number of efforts seek to improve selectivity to monohalogenated methanes, especially methyl chloride, over halogenated methanes with two or more halogen atoms (e.g. methylene chloride). A generic representation of oxidation appears in Formula 1 below.

$$HX + \tfrac{1}{2}O_2 + CH_4 \rightarrow CH_3X + H_2O \qquad \text{(Formula 1)}$$

Several patent publications teach oxidative halogenation of methane using a variety of catalysts. Early oxidative halogenation processes, such as those disclosed in U.S. Pat. No. 4,769,504 to Noceti et al. and U.S. Pat. No. 4,795,843 to Imai et al., tend to produce a large fraction of perhalogenated product (e.g. carbon tetrachloride), something that typically has a lower value than monohalogenated product (e.g. $CH_3Cl$). Such processes also tend to produce an unacceptable quantity of deep oxidation products (nominally $CO_x$, with carbon monoxide (CO) and carbon dioxide ($CO_2$) serving as specific examples). Production of such deep oxidation products wastes a $C_1$ (one carbon atom) hydrocarbon feed such as $CH_4$ and creates challenges such as product separation and by-product disposal.

U.S. Pat. No. 6,452,058 to Schweizer et al. discloses an oxidative halogenation process that comprises contacting a reactant hydrocarbon selected from $CH_4$, a halogenated $C_1$ hydrocarbon, or a mixture thereof with a source of halogen (e.g. hydrogen chloride) and, optionally, a source of oxygen (e.g. molecular oxygen) in conjunction with a catalyst under process conditions sufficient to prepare a halogenated $C_1$ hydrocarbon with a greater number of halogen substituents than the reactant hydrocarbon. The catalyst is a rare earth halide or rare earth oxyhalide that is substantially free of iron and copper. The oxidative halogenation preferably yields essentially no perhalogenated $C_1$ hydrocarbon and low levels, if any, of "undesirable" oxygenates such as CO and $CO_2$.

U.S. Pat. No. 6,452,058 (Schweizer et al.) also refers to a second route to convert methane to halogenated methane by using elemental halogen over a supported acid or platinum metal catalyst, citing U.S. Pat. No. 4,523,040 (Olah) and U.S. Pat. No. 5,354,916 (Horvath et al.). Alternate labels for the second primary route include direct halogenation or electrophilic halogenation. Formula 2 below provides a generic representation of the second route.

$$CH_4 + X_2 \rightarrow CH_3X + HCl \qquad \text{(Formula 2)}$$

Patent Cooperation Treaty (PCT) Application WO 2006/118935 to Podkolzin et al. provides teachings about oxidative halogenation of a reactant hydrocarbon (e.g. $CH_4$, a halogenated $C_1$ hydrocarbon (e.g. $CH_3Cl$ or $CH_2Cl_2$) or a mixture thereof) with a source of halogen and a source of oxygen at a molar ratio of reactant hydrocarbon to the source of halogen in a feed to the reactor in excess of 23:1 and/or at a molar ratio of reactant hydrocarbon to the source of oxygen in excess of 46:1 using a rare earth halide or rare earth oxyhalide catalyst.

WO 03/057318 to WeCkhuysen et al. teaches hydrolytic destruction of halogenated hydrocarbons such as $CCl_4$ over lanthanide-based solid catalysts in conjunction with steam at a temperature within a range of from 200 degrees centigrade (° C.) to 350° C.

Each of oxidative halogenation and direct or electrophilic halogenation yields methyl halide in some amount and each feeds into downstream reactions that yield, among other desirable products, ethylene. Each has favorable features and less than favorable features. Each has at least one reactant and one byproduct that differs from the other. For oxidative halogenation, hydrogen halides (e.g. HCl) serve as a halogen source whereas gaseous halogen (e.g. $Cl_2$) provides halogen for direct halogenation. Oxidative halogenation also requires a source of oxygen, but direct halogenation does not. Oxidative halogenation yields water as a byproduct, while electrophilic halogenation generates hydrogen halide as a byproduct.

Conversion of methyl halide to ethylene involves a reaction represented as Formula 3 below.

$$2CH_3X \rightarrow CH_2{=}CH_2 \text{ or ethylene} + HX \qquad \text{(Formula 3)}$$

Building on the reaction shown in Formula 3, oxidative halogenation appears to be self-contained in that, at least when producing a higher hydrocarbon such as ethylene as a downstream or second step subsequent to preparation of a methyl halide, hydrogen halide from the second step may be used in preparing the methyl halide. Preferred results follow with complete conversion of HX to $CH_3X$ to avoid formation of wet or aqueous HX. Electrophilic or direct halogenation, on the other hand, requires one to reconstitute the halogen in a reaction represented by Formula 4 below. In each instance noted herein, X represents a halogen such as chlorine (Cl).

$$2HX + \tfrac{1}{2}O_2 \rightarrow X_2 + H_2O \qquad \text{(Formula 4)}$$

In some embodiments, this invention is a process for oxidatively halogenating $CH_4$, which process comprises contacting a feed stream that comprises $CH_4$, a source of halogen, and a source of oxygen with a first catalyst and under conditions sufficient to provide a product stream that has a greater selectivity to methyl halide and CO than to methylene halide, trihalomethane or carbon tetrahalide, the first catalyst being selected from a group consisting of solid super acids and solid super bases. The halogen is preferably chlorine such that selectivity to $CH_3Cl$ and CO exceeds selectivity to $CH_2Cl_2$, $CHCl_3$ or $CCl_4$.

In some embodiments of this invention, the feedstream also contacts a second catalyst that oxidatively halogenates at least a portion of the $CH_4$ to yield a mixture comprising at least two members of a group consisting of methyl halide, methylene halide, trihalomethane, carbon tetrahalide, water, hydrogen halide (e.g. HCl), unreacted halogen, and unreacted oxygen. The second catalyst is preferably selected from a group consisting of rare earth halides and rare earth oxyhalides.

In some embodiments of this invention, the feedstream contacts the second catalyst before it contacts the first catalyst, such that contact with the second catalyst yields the mixture of at least two members of a group consisting of methyl halide, methylene halide, trihalomethane, carbon tetrahalide, water, hydrogen halide, unreacted halogen, and unreacted oxygen, and contact with the first catalyst converts at least a portion of the methylene halide, trihalomethane and carbon tetrahalide to carbon monoxide, hydrogen halide and water. While the first and second catalysts may be spatially separated to provide sequential contact, the first and second catalysts may also comprise a catalyst admixture.

In some embodiments of this invention, the product mixture is an equimolar mixture of CO and $CH_3Cl$ and the equimolar mixture contacts a carbonylation catalyst under conditions sufficient to convert at least a portion of the equimolar mixture to at least one of acetyl chloride and acetic acid. In a preferred variation of such embodiments, remove at least a portion of water produced through contact with the first and second catalysts before placing the equimolar mixture in contact with the carbonylation catalyst.

When ranges are stated herein, as in a range of from 2 to 10, both end points of the range (e.g. 2 and 10) and each numerical value, whether such value is a rational number or an irrational number, are included within the range unless otherwise specifically excluded.

Unless stated to the contrary, implicit from the context, or customary in the art, all parts and percents are based on weight. Expressions of temperature may be in terms either of degrees Fahrenheit (° F.) together with its equivalent in ° C. or, more typically, simply in ° C.

"Conversion" or "cony" means mole percentage of $CH_4$ that is converted to all products including halogenated methanes (e.g. $CH_3Cl$, $CH_2Cl_2$, $CHCl_3$ or $(CCl_4)$) and oxygenated by-products (e.g. CO or $CO_2$) in accord with various embodiments of this invention into product(s).

"Selectivity" or "sel" means mole percentage of $CH_4$ that is converted into a specific product, such as a halogenated $C_1$ hydrocarbon product (e.g. $CH_3Cl$) or oxygenated by-product (e.g. CO) divided by the mole percentage of all products produced. For example, determine selectivity for a particular halogenated methane (e.g. $CH_3Cl$) relative to all halogenated methanes present as reaction products (e.g. $CH_3Cl$, $CH_2Cl_2$, $CHCl_3$ and $CCl_4$ where the halogen in chlorine) by multiplying 100 times a quotient determined using moles of the particular halogenated methane (e.g. $CH_3Cl$) as a numerator and moles of all halogenated methanes (e.g. $CH_3Cl$, $CH_2Cl_2$, $CHCl_3$ and $CCl_4$) as a denominator.

In oxidative halogenation processes of various embodiments of this invention, a halogenated $C_1$ hydrocarbon product, preferably a monohalogenated $C_1$ hydrocarbon product, more preferably a monohalogenated methane product, and still more preferably a monochlorinated methane product (e.g. $CH_3Cl$) predominates over further halogenated products (e.g. $CH_2Cl_2$, $CHCl_3$ and $CCl_4$ when the halogen is Cl).

Illustrative solid super acids include tungstated zirconia or tungsten oxide on a zirconia support ($WO_3/ZrO_2$), sulfated zirconia ($SO_4/ZrO_2$), sulfated titania ($SO_4/TiO_2$), sulfated titania-lanthana ($SO_4/TiO_2$—$La_2O_3$), sulfated tin oxide ($SO_4/SnO_2$), cerium sulfate on a zirconia support ($Ce(SO_4)_2/ZrO_2$), and vanadium sulfate on a zirconia support ($VSO_4/ZrO_2$). As used herein, placement of $ZrO_2$ right of a diagonal slash (/) means $ZrO_2$ serves as both a catalyst support for catalytic materials shown left of the diagonal slash and as an integral component of the catalyst itself. The solid super acid is preferably $SO_4/ZrO_2$.

Illustrative solid super bases include calcium fluoride on a zirconia support ($CaF_2/ZrO_2$), barium fluoride on a zirconia support ($BaF_2/ZrO_2$); potassium-doped magnesium oxide (K-doped/MgO); and sodium oxide on a magnesium oxide support ($Na_2O/MgO$). The solid super base is preferably $CaF_2/ZrO_2$.

The source of oxygen can be any oxygen-containing gas or mixture of such gases. Illustrative oxygen-containing gases include essentially pure or molecular oxygen, air, oxygen-enriched air, or a mixture of oxygen with a diluent gas that does not interfere with oxidative halogenation. The diluent gas is preferably at least ($\geq$) one gas selected from a group consisting of nitrogen, argon, helium, carbon monoxide, carbon dioxide, and methane. For mixtures of oxygen and diluent gas, the diluent gas is present in an amount of $\geq 10$ mole percent (mol %), based upon total moles of methane, source of halogen, source of oxygen and diluent. The amount of diluent gas preferably does not exceed ($\leq$) 90 mol %, based upon total moles of methane, source of halogen, source of oxygen and diluent.

The source of oxygen is present in an amount that satisfies two criteria. First, the amount must be sufficient to yield the desired methyl halide as the predominant halogenated product, especially with relation to methylene halide, and with a desired degree of selectivity to the desired methyl halide relative to all other reaction products including methylene halide, trihalomethane and tetrahalomethane as halogenated reaction products and CO and $CO_2$ as non-halogenated reaction products. Second, the amount is sufficient to provide a "fuel-rich" mixture of source of oxygen and fuel, in this case methane, for reasons of safety, and preferably falls outside a fuel-rich flammability limit for a mixture of methane and source of oxygen.

In some embodiments of this invention, the conditions sufficient to provide a product stream that has a greater selectivity to methyl halide and CO than to methylene halide, trihalomethane and methane tetrahalide include a feedstream flow rate sufficient to minimize conversion of methyl halide to CO and hydrogen halide. A preferred feedstream flow rate is a weight hourly space velocity (WHSV) within a range of from 0.1 gram (g) of total feed of methane, source of halogen, source of oxygen and optional diluent per g of catalyst per hour to less than (<) 100 g of total feed of methane, source of halogen, source of oxygen and, when present, diluent per g of catalyst per hour.

The source of halogen is preferably $\geq$ one hydrogen halide selected from hydrogen chloride (HCl), hydrogen bromide, hydrogen fluoride, and hydrogen iodide. The halogen is preferably chlorine and the source of halogen is preferably hydrogen chloride.

The halide, while most preferably chloride, may also be a bromide, iodide or fluoride as in hydrogen bromide, hydrogen iodide or hydrogen fluoride. If the halide is other than a chloride, illustrative monohalogenated products are methyl bromide, methyl iodide and methyl fluoride. A mixture of hydrogen chloride and, for example, hydrogen bromide conceivably produces a mixture of methyl chloride and methyl bromide, should such a mixture be desired.

The source of halogen is preferably present in an amount that yields a desired methyl halide product as a predominant halogenated product, whether viewing halogenated products alone or in combination with oxygenates of carbon, specifically CO and $CO_2$. The amount typically varies depending upon process-related parameters such as specific process stoichiometry, process conditions (e.g. reactant flow rate and reaction temperature) and choice of catalyst (e.g. solid super acid or solid super base).

The aforementioned conditions preferably comprise at least one of a temperature within a range of from 200° C. to 600° C. and a pressure within a range of from 95 kilopascals (kPa) to 1100 kPa.

In some embodiments of this invention, the conditions are sufficient to produce an equimolar mixture of CO and $CH_3Cl$. Alternatively, the feedstream may further comprise an amount of CO sufficient to provide an equimolar mixture of CO and $CH_3Cl$.

In some embodiments of this invention, the equimolar mixture of CO and $CH_3Cl$ contacts a carbonylation catalyst under conditions sufficient to convert at least a portion of the equimolar mixture to at least one of acetyl chloride and acetic acid. The carbonylation catalyst is preferably a rhodium on carbon catalyst. Removing water prior to contact with the carbonylation catalyst represents a preferred variation of such embodiments.

Selectivity to methyl halide preferably falls within a range of from 35 mol % to 100 mol %, based upon moles of halogenated products present in the product stream. The range is more preferably from 50 mol % to 99 mol %, based upon moles of halogenated products present in the product stream. The range is still more preferably from 75 mol % to 98 mol %, based upon moles of halogenated products present in the product stream.

Conversion of methane to methyl halide preferably falls within a range of from 0.1 mol % to 100 mol %, based upon moles of methane present prior to conversion. The range is more preferably from one (1) mol % to 75 mol %, based upon moles of methane present prior to conversion. The range is still more preferably from five (5) mol % to 50 mol %, based upon moles of $CH_4$ present prior to conversion.

In some embodiments of this invention, selectivity to a combination of methyl halide and CO preferably falls within a range of from 50 mol % to 100 mol %. The range is more preferably from 75 mol % to 97 mol %, and still more preferably from 90 mol % to 95 mol %.

In some embodiments of this invention, selectivity to methyl halide, relative to selectivity to a combination of methyl halide, methylene halide, trihalomethane and carbon tetrahalide preferably falls within a range of from 85 mol % to 100 mol %. The range is more preferably from 90 mol % to 100 mol %, and still more preferably from 95 mol % to 100 mol %.

The process of various embodiments of this invention preferably yields essentially no perhalogenated product, such as $CCl_4$ when the desired product is $CH_3Cl$. As used herein, "essentially no perhalogenated product" means production of <five mol % of perhalogenated product, preferably <two mol %, more preferably one mol %, and still more preferably no more than 0.1 mol %, each mol % being based upon total moles of halogenated product.

Oxidative halogenation can be conducted in a reactor of any conventional design suitable for gas phase processes, including batch, fixed bed, fluidized bed, transport bed, continuous and intermittent flow reactors, and catalytic distillation reactors. Process conditions (e.g., molar ratio of feed components, temperature, pressure, gas hourly space velocity (GHSV)), can be varied widely, provided they the desired halogenated methane product, preferably $CH_3Cl$. Typically, the process temperature is greater than (>) 200° C., preferably >300° C., and more preferably >350° C. Typically, the process temperature is <600° C., preferably, <500° C., and more preferably, <450° C. Ordinarily, the process can be conducted at atmospheric pressure; but operation at higher or lower pressures is possible, as desired. Preferably, the pressure is ≥14 pounds per square inch absolute (psia) (97 kilopascals (kPa)), but <300 psia (2,068 kPa). Typically, the total weight hourly space velocity (WHSV) of the feed (methane, source of halogen, source of oxygen, and optional diluent) will be >0.1 gram total feed per g catalyst per hour ($h^{-1}$), and preferably, >0.5 $h^{-1}$. Typically, the total WHSV of the feed will be <100 $h^{-1}$, and preferably, <20 $h^{-1}$.

Monohalogenated and dihalogenated hydrocarbon products, preferably, monohalogenated products, more preferably, $CH_3Cl$ or methyl bromide, produced in the oxidative halogenation process of this invention can be utilized as a feed in downstream processes that produce high-value commodity chemicals, such as methyl alcohol, dimethyl ether, light olefins, including ethylene, propylene, and butenes; higher hydrocarbons, including C5+ gasolines; vinyl halide monomer, and acetic acid. The hydrolysis of methyl halides to form methyl alcohol is described in the art, representative citations of which include U.S. Pat. No. 1,086,381 (Masland), U.S. Pat. No. 4,990,696 (Stauffer), U.S. Pat. No. 4,523,040 (Olah), and U.S. Pat. No. 5,969,195 (Stabel et al.), as well as G. Olah in *Journal of the American Chemical Society,* 1985, 107, 7097-7105, and I. Fells, *Fuel Society Journal,* 10, (1959), pages 26-35. Methyl chloride hydrolysis to methyl alcohol can be represented by the following stoichiometric reaction: $CH_3Cl+H_2O\rightarrow CH_3OH+HCl$.

Methyl halide, preferably $CH_3Cl$, prepared by the aforementioned oxidative halogenation of $CH_4$ can be condensed to form light olefins, such as ethylene ($CH_2=CH_2$), propylene, butenes, and higher hydrocarbons, including $C_{5+}$ gasolines. Such a condensation reaction may be represented by the following equation showing condensation to $CH_2=CH_2$ with hydrogen chloride (HCl) as a co-product that can be recycled for use in oxidative halogenation as a source of halogen:

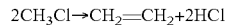

$2CH_3Cl\rightarrow CH_2=CH_2+2HCl$

Any catalyst capable of effecting condensation can be employed. U.S. Pat. No. 5,397,560 (Millar et al.), for example, discloses the use of aluminosilicates having a DCM-2 structure code for the conversion of methyl halides into light olefins, predominantly ethylene and propylene.

EXAMPLES

Examples (Ex) of the present invention are designated by Arabic numerals and Comparative Examples (Comp Ex or CEx) are designated by capital alphabetic letters. Unless otherwise stated herein, "room temperature" and "ambient temperature" are nominally 25° C.

($SO_4/ZrO_2$ Preparation A

Heat two liters (2 L) of deionized (DI) water that is adjusted to a pH of 10 with ammonium hydroxide ($NH_4OH$) to a set point temperature of 50° C. Dissolve 65.1 g (0.202 mole) of hydrated zirconium oxychloride ($ZrOCl_2.8\ H_2O$) in the heated and pH-adjusted DI water then add sufficient DI water to increase solution volume to 250 milliliters (mL). Transfer the resulting solution to a first addition funnel.

Dilute 140 g of concentrated $NH_4OH$ with 500 mL of DI water and transfer the diluted $NH_4OH$ to a second addition funnel.

Over a period of 15 minutes, add contents of the first and second addition funnels to a one (1) L container having water adjusted to a pH of 10 with $NH_4OH$ disposed therein such that, at the conclusion of the period of 15 minutes, the container has disposed therein one volume of the contents of the first addition funnel for every two volumes of the contents of the second addition funnel. Maintain container contents pH at 10 by adding concentrated $NH_4OH$ as needed. Stir container contents for a period of one hour, then allow precipitated solids (determined to be zirconium oxyhydrate ($ZrO(OH)_2$)) to settle to the container's bottom.

Recover the precipitated solids via four iterations of filtration and re-suspension of the solids in one L of DI water followed by a final filtration. Dry the solids overnight in an air oven operating at a set point temperature of 110° C. After drying, crush the solids to a mesh size of 14/30 (between 0.6 nanometers (nm) and 1.2 mm).

Dry 23 g of crushed solids for one hour in an air oven operating at a set point temperature of 140° C. to remove residual surface water. Add 25 g of concentrated (18 normal (N)) sulfuric acid ($H_2SO_4$) to DI water to prepare 100 mL of a 2.55 M $H_2SO_4$ solution. Impregnate the dried, crushed solids with 7.49 g of the 2.55 M $H_2SO_4$ solution.

Calcine the impregnated solids in an air oven as follows: a) heat the impregnated solids from a set point temperature of 25° C. to a set point temperature of 125° C. over a period of one hour; b) maintain the 125° C. temperature for a period of two hours; c) increase the set point temperature to 600° C. over a period of four hours; d) maintain the 600° C. temperature for four hours; e) cool to a set point temperature of 130° C. over a period of three hours; 0 hold at the 130° C. temperature until removing the calcined solids from the oven; and g) cool the calcined solids to ambient temperature in a dessicator. Calcined solids removed from the dessicator have a weight of 20.5 g and have a sulfate content of six (6) wt %, based upon total calcined solids weight and the amount of sulfuric acid added.

(e.g. helium (He), nitrogen ($N_2$) or a combination thereof) through each of the tubes at temperatures (Temp) shown in Table 1 below and determine percent conversion $CH_4$ to $CH_3Cl$ at each of the temperatures, with such conversions also shown in Table 1 below. Table 2 below shows selectivity to $CH_3Cl$, $CH_2Cl_2$ and $CHCl_3$ data for Ex 1.

TABLE 1

| | Ex or CEx | |
|---|---|---|
| Temp (° C.) | CEx A | Ex 1 |
| 375 | 2.7 ± 0.4 | 2.4 ± 0.4 |
| 400 | 5.5 ± 0.3 | 5.8 ± 0.3 |
| 425 | 8.8 ± 0.8 | 9.0 ± 0.7 |
| 450 | 11.1 ± 0.5 | 12.9 ± 0.5 |
| 475 | 17.9 ± 0.2 | 20.2 ± 0.2 |

The data in Table 1 demonstrate that, at least at temperatures of 450° C. and 475° C., addition of a layer of sulfated zirconia to a layer of LaOCl (Ex 1) provides an increase in conversion of $CH_4$ to $CH_3Cl$ relative to a single layer of LaOCl. At temperatures of 375° C., 400° C. and 425° C., no significant difference in conversion of $CH_4$ to $CH_3Cl$ exists between Ex 1 and CEx A.

TABLE 2

| | Ex or CEx Selectivity | | | | | |
|---|---|---|---|---|---|---|
| Temp (° C.) | A ($CH_3Cl$) | 1 ($CH_3Cl$) | A ($CH_2Cl_2$) | 1 ($CH_2Cl_2$) | A ($CHCl_3$) | 1 ($CHCl_3$) |
| 375 | 96.8 ± 0.3 | 100.0 ± 0.3 | 3.2 ± 0.3 | 0.0 ± 0.3 | 0.02 ± 0.01 | 0.0 ± 0.01 |
| 400 | 92.8 ± 0.3 | 100.0 ± 0.3 | 7.0 ± 0.3 | 0.0 ± 0.03 | 0.19 ± 0.03 | 0.0 ± 0.03 |
| 425 | 88.9 ± 0.7 | 99.8 ± 0.6 | 10.5 ± 0.6 | 0.2 ± 0.6 | 0.62 ± 0.06 | 0.0 ± 0.05 |
| 450 | 85.1 ± 0.5 | 99.5 ± 0.5 | 13.8 ± 0.4 | 0.5 ± 0.5 | 1.15 ± 0.06 | 0.0 ± 0.07 |
| 475 | 77.7 ± 0.1 | 99.2 ± 0.1 | 20.0 ± 0.1 | 0.8 ± 0.8 | 2.30 ± 0.02 | 0.0 ± 0.02 |

$SO_4/ZrO_2$ Preparation B

Replicate $SO_4/ZrO_2$ Preparation A with changes. First, calcine 23 g of the sieved and dried $ZrO(OH)_2$ solids for one hour in air in an oven operating at a set point temperature of 300° C. to convert the $ZrO(OH)_2$ to $ZrO_2$. Second add 25 g of concentrated (approximately 18 N)) sulfuric acid ($H_2SO_4$) to DI water to make 100 ml of a 2.55 M $H_2SO_4$ solution. Third, impregnate the $ZrO_2$ with 7.51 g of the $H_2SO_4$ solution. Fourth, calcine as in Preparation A to yield 20.5 g of a nominal six percent by weight (6 wt %) sulfated zirconia ($SO_4/ZrO_2$).

Ex 1 and CEx A

In a first upflow reactor tube (Ex 1) having an internal diameter of four (4) millimeters (mm), first place a layer of 0.5 g of lanthanum oxychloride (LaOCl) (prepared using teachings of U.S. Pat. No. 6,452,058 (Schweizer et al.)) proximate to the tube's midpoint, then place a layer of 0.5 g of the sulfated zirconia prepared above on top of the LaOCl layer so that flowing reactant gases first contact the LaOCl layer and then contact the sulfated zirconia layer. In a second upflow reactor tube (CEx A), place only the layer of 0.5 g of LaOCl as in Ex 1.

Pass a feedstream (20 volume percent (vol %) $CH_4$, 20 vol % HCl, 10 vol % oxygen ($O_2$) and 50 vol % inert gases The data presented in Table 2 demonstrate that at all temperatures shown in Table 2, adding a layer of sulfated zirconia to a layer of LaOCl (Ex 1) effectively increases selectivity to monochlorinated methane ($CH_3Cl$) relative to multichlorinated methanes ($CH_2Cl_2$ and $CHCl_3$) in comparison to a single layer of LaOCl (CEx A) even if it does not, as shown in Table 1 above, increase conversion of methane to $CH_3Cl$ relative to that same single layer of LaOCl at temperatures of 375° C., 400° C. and 425° C.

Ex 2-4 and CEx B-C

Replicate Ex 1 at a temperature of 475° C. and determine selectivity to $CH_3Cl$, $CH_2Cl_2$ and CO, on a mole basis to $CH_3Cl$, $CH_2Cl_2$ and CO, as well as relative selectivity to $CH_3Cl$ and $CH_2Cl_2$, based upon moles of $CH_3Cl$ and $CH_2Cl_2$. Report results in Table 3 below, with selectivity to $CH_3Cl$, $CH_2Cl_2$ and CO shown left of a blank column and selectivity to $CH_3Cl$ and $CH_2Cl_2$ shown left of the blank column. CEx B uses only 0.5 g of sulfated zirconia. Ex 4 represents a less preferred arrangement that reverses the order layer shown in Ex 1 above. Ex 2 mixes the LaOCl and sulfated zirconia in a single layer. Ex 3 uses the same catalyst arrangement as in Ex 1. CEx C uses the same catalyst arrangement as CEx A

TABLE 3

| Ex or CEx | Component | | | | |
|---|---|---|---|---|---|
| | $CH_3Cl$ | $CH_2Cl_2$ | CO | $CH_3Cl$ | $CH_2Cl_2$ |
| B | 37.5 | 0.69 | 61.8 | 98.19 | 1.81 |
| 2 | 52.6 | 2.4 | 43.6 | 95.64 | 4.36 |
| 3 | 36.8 | 0.29 | 57.9 | 99.22 | 0.78 |
| 4 | 46 | 2.7 | 46.7 | 94.46 | 5.54 |
| C | 65.5 | 16.6 | 15.2 | 79.78 | 20.22 |

The data presented in Table 3 demonstrate that use of a solid super acid ($SO_4/ZrO_2$) improves selectivity to $CH_3Cl$ over selectivity to $CH_2Cl_2$ relative to selectivity to $CH_3Cl$ over selectivity to $CH_2Cl_2$ when using LaOCl alone (CEx C). In fact, the solid super acid by itself (CEx B) provides an improvement in selectivity over LaOCl alone (CEx C). Maximum increase in selectivity to $CH_3Cl$ over selectivity to $CH_2Cl_2$ occurs when a feedstream first contacts a layer of LaOCl before contacting a solid super acid layer (Ex 3). A mixture of solid super acid and LaOCl (Ex 2), while not as good as the arrangement of Ex 3, still produces better results than LaOCl alone (CEx C) as does Ex 4, with a reversal of the layer arrangement of Ex 3.

Ex 5-Ex 6, and CEx D

Use a reactor system that consists of five reactor tubes immersed in a common sand bath heater with 1.50 g of LaOCl (prepared using teachings of U.S. Pat. No. 6,452,058 (Schweizer et al.)) in one tube (CEx D), 1.51 g of $SO_4/ZrO_2$ Preparation B catalyst in a second tube (Ex 5), and 1.51 g of $SO_4/ZrO_2$ Preparation A catalyst in a third tube (Ex 6). The fourth and fifth tubes are empty. Feed, at a rate of 33 standard cubic centimeters per minute (sccm), a mixture of gases via mass flow controllers to the reactor system to provide a gaseous mixture of 20 vol % $CH_4$, 20 vol % HCl, and 10 vol % $O_2$, 5 mol % nitrogen ($N_2$), and 45 vol % helium, each vol % being based upon total volume of gas present in the gaseous mixture. As used herein with respect to gases, vol % equals mole percent (mol %). Reactor tube content analysis for $CH_4$, $CH_3Cl$ (MeCl), $CH_2Cl_2$ (MeCl$_2$), CO and $CO_2$ occurs via gas phase chromatography using a Siemens Maxum™ Edition II Process Gas Chromatograph. Table 4 below shows analytical results of gaseous reactor tube contents at a temperature of 430° C.

Ex 7-Ex 8 and CEx E

Replicate Ex 5, Ex 6 and Comp Ex D, respectively for Ex 7, Ex 8 and Comp Ex E, but change the temperature to 480° C. See Table 5 below for analytical results of gaseous reactor tube contents.

The results in Table 4 and Table 5 support several observations. First, each of the catalysts used in Ex 5 through Ex 8 convert at least a portion of $CH_4$ to $CH_3Cl$ with varying selectivity to $CH_3Cl$ as do CE-D and CE-E. In each case, selectivity to $CH_3Cl$ exceeds selectivity to $CH_2Cl_2$. Second, each of the catalysts of Ex 5-8 produces some amount of carbon oxides (CO and $CO_2$) as do CE-D and CE-E. However, each of the catalysts of Ex 5-8 exhibit a combined selectivity of $CH_3Cl+CO$ greater than 84%, whereas CE-D and CE-E exhibit a combined selectivity of $CH_3Cl+CO$ less than 84%. Third, each of the catalysts of Ex 5-8 exhibits a relative $CH_3Cl$ selectivity greater than 95% whereas CE-E and CE-E exhibit a relative $CH_3Cl$ selectivity less than 81%.

Although many embodiments of this process are possible, Ex 3 and Comp Ex B from Table 3 show particularly high selectivity (>96%) to monohalogenated methane relative to methylene halide. The data in Tables 4 and 5 show that the catalyst and catalyst configurations of Ex 5-Ex 8 show high selectivity to monohalogenated methane ($CH_3Cl$). Nonetheless, conversion for an equal weight of catalyst is inferior to that of the catalyst in Comp Ex D and E. If one elects to maximize selectivity to monohalogented methane, then the arrangement of Ex 3 (feedstream contacts LaOCl layer and feedstream with reacted components then contacts a solid super acid layer) presents a preferred option over that of CEx B, CEx C or CEx D. The catalyst composition and arrangement of Ex 3 leads to both higher activity and higher selectivity to monohalogenated methane relative to using each individual catalyst separately (CEx B-CEx D).

Ex 9-Ex 14

Replicate Ex 5, but vary gas flow rate (in sccm), and GHSV as shown in Table 6 below. Ex 9-12 use 1.51 g of the $SO_4/ZrO_2$ Preparation B catalyst. Ex 12 and Ex 14 use 3.02 g of the same catalyst. Table 6 also shows analytical results of gaseous reactor tube contents.

Ex 15-Ex 20

Replicate Ex 9-14, but use 1.51 g of the $SO_4/ZrO_2$ Preparation A catalyst for Ex 15 through Ex 18 and 2.99 g of the same catalyst for Ex 19 and Ex 20. Table 7 below shows gas flow rate, GHSV and analytical results of gaseous reactor tube contents.

TABLE 4

| Ex/CE | $CH_4$ conv | MeCl Sel (mol %) | MeCl$_2$ Sel mol % | MeCl$_3$ Sel (mol %) | CO Sel mol % | $CO_2$ Sel (mol %) | MeCl + CO Sel (mol %) | Rel MeCl Sel (mol %) | Rel MeCl$_2$ (mol %) | Rel MeCl$_3$ (mol %) |
|---|---|---|---|---|---|---|---|---|---|---|
| D | 15 | 70.5 | 15.4 | 1.4 | 12.6 | 0.5 | 83.1 | 80.8 | 17.6 | 1.6 |
| 5 | 7.9 | 64.1 | 0 | 0 | 33.6 | 2.5 | 97.7 | 100.0 | 0.0 | 0.0 |
| 6 | 6.3 | 68.0 | 0 | 0 | 30.8 | 1.6 | 98.8 | 100.0 | 0.0 | 0.0 |

TABLE 5

| Ex/CE | $CH_4$ conv | MeCl sel (mol %) | MeCl$_2$ sel mol % | MeCl$_3$ sel (mol %) | CO sel (mol %) | $CO_2$ sel (mol %) | MeCl + CO (mol %) | Rel MeCl (mol %) | Rel MeCl$_2$ (mol %) | Rel MeCl$_3$ (mol %) |
|---|---|---|---|---|---|---|---|---|---|---|
| E | 33.4 | 50.5 | 24.2 | 2.5 | 20.7 | 2.1 | 71.2 | 65.4 | 31.3 | 3.3 |
| 7 | 30.3 | 8.8 | 0.4 | 0 | 75.7 | 15.1 | 84.5 | 95.2 | 4.8 | 0.0 |
| 8 | 27.8 | 17.2 | 0.3 | 0 | 73.6 | 9 | 90.8 | 98.3 | 1.7 | 0.0 |

TABLE 6

| Ex No | Flow (sccm) | GHSV (hr$^{-1}$) | CH4 Conv (mol %) | O2 Conv (mol %) | CO Sel (mol %) | CO2 Sel (mol %) | MeCl Sel (mol %) | MeCl$_2$ Sel (mol %) | MeCl + CO Sel (%) | Rel MeCl Sel (%) | Rel MeCl$_2$ Sel (%) |
|---|---|---|---|---|---|---|---|---|---|---|---|
| 9  | 33  | 1320 | 29   | 79.6 | 65.3 | 14.8 | 19.5  | 0.44 | 84.5 | 97.79 | 2.21 |
| 10 | 50  | 2000 | 25.8 | 67.2 | 64.6 | 9.95 | 24.9  | 0.47 | 89.5 | 98.15 | 1.85 |
| 11 | 69  | 2760 | 23.3 | 57.1 | 60.9 | 7.07 | 31.5  | 0.55 | 92.4 | 98.28 | 1.72 |
| 12 | 105 | 4200 | 23   | 54.1 | 57.7 | 6.4  | 35.2  | 0.71 | 92.9 | 98.02 | 1.98 |
| 13 | 33  | 660  | 30.8 | 94.7 | 65.1 | 25.3 | 9.61  | 0    | 74.7 | 100   | 0    |
| 14 | 50  | 1000 | 27.7 | 78.1 | 67.8 | 16.1 | 16.05 | 0    | 83.9 | 100   | 0    |

TABLE 7

| Ex/CE No | Flow (sccm) | GHSV (h$^{-1}$) | CH4 Conv (mol %) | O2 Conv (mol %) | CO Sel (mol %) | CO2 Sel (mol %) | MeCl Sel (mol %) | MeCl$_2$ Sel (mol %) | MeCl + CO Sel (%) | Rel MeCl Sel (%) | Rel MeCl$_2$ Sel (%) |
|---|---|---|---|---|---|---|---|---|---|---|---|
| 15 | 33  | 1320 | 23.7 | 57.8 | 62.1 | 8.05 | 29.6 | 0.3 | 91.7 | 98.9 | 1.1 |
| 16 | 50  | 2000 | 20.4 | 45.8 | 54.2 | 4.8  | 40.7 | 0.4 | 94.9 | 99.1 | 0.9 |
| 17 | 69  | 2760 | 18.8 | 49.6 | 49.8 | 3.6  | 46.3 | 0.3 | 96.1 | 99.3 | 0.7 |
| 18 | 105 | 4200 | 17.6 | 33.9 | 46.7 | 2.6  | 50.1 | 0.5 | 96.8 | 99.1 | 0.9 |
| 19 | 33  | 660  | 25.5 | 68.7 | 75.7 | 8.1  | 16.2 | 0   | 91.9 | 100  | 0   |
| 20 | 50  | 1000 | 21.4 | 52.1 | 67.6 | 4.8  | 27.6 | 0   | 95.2 | 100  | 0   |

The results in Table 6 and Table 7 support several observations. First, each of the catalysts used in Ex 8 through Ex 19 convert at least a portion of $CH_4$ to $CH_3Cl$ with varying selectivity to $CH_3Cl$. In each case, selectivity to $CH_3Cl$ exceeds selectivity to $CH_2Cl_2$. Second, each of the catalysts of Ex 8-19 produce some amounts of carbon oxides (CO and $CO_2$). However, each of the catalysts of Ex 8-19 exhibits a combined selectivity of $CH_3Cl$+CO greater than 74%. Fourth, each of the catalysts of Ex 8-19 exhibits a relative $CH_3Cl$ selectivity greater than 97%.

Similar results are expected with other strongly acidic materials and process conditions, all of which are disclosed herein.

Preparation of $CaF_2/ZrO_2$

Part A:

Place two liters (2 L) of deionized water in a 4 L beaker. Adjust pH of the deionized water to 10 by adding ammonium hydroxide ($NH_4OH$) to form a first solution. Heat the first solution to a temperature of 40 degrees centigrade (° C.).

Dissolve 65.1 grams (g) (0.202 moles (mol)) of hydrated zirconium oxychloride ($ZrOCl_2.8H_2O$) in 100 milliliters (ml) of deionized water, then add sufficient deionized water to yield 250 ml of a second solution. Place the second solution in a first addition funnel.

Dilute 140 g of concentrated (approximately 15 molar (M)) $NH_4OH$ with 500 ml of deionized water to yield 500 ml of a third solution. Place the third solution in a second addition funnel.

Add the second and third solutions to the first solution with rapid (greater than (>) 250 revolutions per minute (rpm)) stirring over a period of 15 minutes at rates sufficient to add one volume of the second solution for every two volumes of the third solution. Add additional concentrated $NH_4OH$ to maintain beaker contents at a pH of 10. Continue stirring beaker contents for a period of 30 minutes, then stop stirring and allow precipitated solids (zirconium oxyhydroxide ZrO$(OH)_2$) to settle to the beaker's bottom.

Part B:

Dissolve 3.62 g of calcium chloride ($CaCl_2$) in 100 ml of deionized water to form a fifth solution and 3.98 g of potassium fluoride (KF) in 100 ml of deionized water to form a sixth solution.

Add the fifth and sixth solutions to contents of the beaker with rapid stirring (>250 rpm), then increase temperature of the beaker contents to 40° C. and continue stirring for four and one half hours before allowing temperature to return to ambient and solid components of the beaker contents to settle to the bottom of the beaker. Settling occurs over a period of from about one-half hour to one hour. Keep the settled contents in supernatant prior to starting recovery of solid components.

Recover solid components from the beaker contents via filtration and then resuspend the solid components in 1 L of deionized water with stirring for 15 minutes before recovering solids again via filtration. Repeat resuspension and filtration four times or until analysis of resuspended solids using silver nitrate ($AgNO_3$) reveals no detectable chlorine ions ($Cl^-$), then filter one more time. Dry solids collected via filtration at a temperature of 110° C. for two hours, then break up the solids and continue drying for an additional 10 hours at a temperature of 115° C. Calcine the dried solids in an air oven heated at a set point temperature of 800° C. for five hours, then hold the calcined solids for an additional period of four hours before allowing the calcined solids to cool to ambient temperature. The calcined solids (24.5 g) constitute calcium fluoride on a zirconia support ($CaF_2/ZrO_2$).

Preparation of $WO_3/ZrO_2$

Replicate preparation of $CaF_2/ZrO_2$ through allowing precipitated ZrO$(OH)_2$ solids to settle to the beaker's bottom (through Part A). Dry the precipitated ZrO$(OH)_2$ solids at a temperature of 110° C. for at least 12 hours. Crush and sieve the dried ZrO$(OH)_2$ solids to a 14/30 mesh size (sieve opening range of 1.41 mm for 14 mesh and 0.595 mm for 30 mesh), meaning that solids pass through the 14 mesh screen, but remain on the 30 mesh screen.

Dissolve 2.85 g of ammonium metatungstate ($(NH_4)_6H_2W_{12}O_{40}$) in 7.5 g of deionized (DI) water to provide an ammonium metatungstate solution. Add the ammonium metatungstate solution to 17.5 g of dried (non-calcined) ZrO(OH)$_2$ solids (collected on the 30 mesh (0.595 mm sieve opening) screen via impregnation.

Calcine the impregnated material as follows: heat the solids in an air calcination oven from ambient temperature to a set point temperature of 125° C. over a period of one hour at a heating rate of 1.7° C. per minute; hold the solids at the 125° C. set point temperature for a period of two hours; heat the solids to a set point temperature of 800° C. over a period of 10 hours at a rate of 1.1° C. per minute; hold at 800° C. for a period of four hours; cool to 130° C. over a period of three hours at a rate of 3.7° C. per minute; hold the solids at 130° C. for a period of 4 hours; and remove the solids from the oven and place them in a dessicator for cooling to ambient temperature. The cooled solids (16.4 g) constitute tungstate on a zirconia support ($WO_3/ZrO_2$).

Preparation of $Ce(SO_4)_2/ZrO_2$

Replicate preparation of $WO_3/ZrO_2$, but use cerium sulfate instead of ammonium metatungstate. Dissolve 4.5 g of hydrated cerium sulfate ($Ce(SO_4)_2 \cdot nH_2O$) in 15.5 g of DI water to provide a cerium sulfate solution. Add 5.1 g of the cerium sulfate solution to 13.2 g of dried (non-calcined) ZrO(OH)$_2$ solids via impregnation.

Calcine as in preparation of $CaF_2/ZrO_2$, but change the 800° C. set point temperature to 600° C. and reduce the period of heating to 600° C. to four hours. The cooled solids (11.4 g) constitute cerium sulfate on a zirconia support ($Ce(SO_4)_2/ZrO_2$).

Preparation of $VO(SO_4)/ZrO_2$

Replicate preparation of $Ce(SO_4)_2/ZrO_2$, but use 4.0 g of a vanadium sulfate solution prepared by dissolving 4.5 g of hydrated vanadium sulfate ($VO(SO_4)_2 \cdot nH_2O$) in 15.6 g of DI water in place of cerium sulfate. The cooled solids (10.0 g) constitute vanadium sulfate on a zirconia support ($VO(SO_4)/ZrO_2$).

Preparation of $ZrO(OH)_2$

Replicate preparation of $CaF_2/ZrO_2$ through allowing precipitated $ZrO(OH)_2$ solids to settle to the beaker's bottom (through Part A). Dry the precipitated $ZrO(OH)_2$ solids at a temperature of 110° C. for at least 12 hours. Crush and sieve the dried $ZrO(OH)_2$ solids to a 14/30 mesh size as in preparation of $WO_3/ZrO_2$.

Ex 21-25

Use the same reactor as described for Ex 5, Ex 6 and CEx D and replicate the process used therein, but change the gaseous flow rate to 20 sccm and the gaseous mixture to 80 vol % CH$_4$, 10 vol % HCl, and 5 vol % O$_2$, and 5 vol % N$_2$, each vol % being based upon total volume of gas present in the gaseous mixture. Place 0.5 g of $CaF_2/ZrO_2$ in one tube (Ex 21), 0.5 g of $WO_3/ZrO_2$ in a second tube (Ex 22), 0.5 g of $(CeSO_4)_2/ZrO_2$ in a third tube (Ex 23), 0.5 g of $VO(SO_4)/ZrO_2$ in a fourth tube (Ex 24), and 0.5 g of $SO_4/ZrO_2$ in a fifth tube (Ex 25). See Table 8 below for analytical results of reactor tubes at temperatures specified for each Ex, with conversion and selectivity being as defined above.

TABLE 8

| Ex No | Reaction Temperature (° C.) | CH$_4$ Conv. (mol %) | MeCl Sel. (mol %) | MeCl$_2$ Sel. (mol %) | CO Sel. (mol %) | CO$_2$ Sel. (mol %) | MeCl + CO Sel (mol %) | Rel MeCl Sel (mol %) | Rel MeCl$_2$ Sel (mol %) |
|---|---|---|---|---|---|---|---|---|---|
| 21 | 475 | 5.9 | 82.0 | 4.3 | 10.6 | 3.30 | 92.6 | 95.0 | 5.0 |
| 22 | 430 | 4.9 | 11.5 | 0.0 | 74.0 | 14.35 | 85.5 | 100 | 0.0 |
| 23 | 430 | 6.3 | 63.2 | 1.4 | 28.3 | 7.00 | 91.5 | 97.8 | 2.2 |
| 24 | 430 | 5.5 | 45.8 | 0.4 | 43.8 | 9.93 | 89.6 | 99.1 | 0.9 |
| 25 | 430 | 5.4 | 39.7 | 0.0 | 54.8 | 4.90 | 94.5 | 100.0 | 0.0 |

The results in Table 8 support several observations. First, each of the catalysts used in Ex 21 through Ex 25 convert at least a portion of CH$_4$ to MeCl (CH$_3$Cl) with varying selectivity to MeCl. In each case, selectivity to MeCl exceeds selectivity to MeCl$_2$. Although $CaF_2/ZrO_2$ (Ex 21) and $Ce(SO_4)_2/ZrO_2$ (Ex 23) provide higher MeCl selectivity than the catalysts of Ex 22 ($WO_3/ZrO_2$), Ex 23 ($VO(SO_4)/ZrO_2$) and Ex 25 ($SO_4/ZrO_2$), the catalysts of Ex 22, Ex 24 and Ex 25 are also suitable. Second, each of the catalysts of Ex 21-25 produce some amounts of carbon oxides (CO and CO$_2$), again with Ex 21 and Ex 23 producing the lowest amounts of such carbon oxides. Third, each of the catalysts of Ex 21-25 exhibits a combined selectivity of CH$_3$Cl+CO greater than 85%. Fourth, each of the catalysts of Ex 21-25 exhibits a relative CH$_3$Cl selectivity greater than 95%.

What is claimed is:

1. A process for oxidatively halogenating methane, which process comprises contacting a feed stream that comprises methane, a source of halogen that is at least one hydrogen halide selected from hydrogen chloride, hydrogen bromide, hydrogen fluoride, and hydrogen iodide, and a source of oxygen with a first catalyst and under conditions sufficient to provide a product stream that has a greater selectivity to methyl halide and carbon monoxide than to methylene halide, trihalomethane or carbon tetrahalide, the first catalyst being selected from a group consisting of solid super acids and solid super bases.

2. The process of claim 1, wherein the solid super acid selected from a group consisting of tungstated zirconia, sulfated zirconia, sulfated titania, sulfated titania-lanthana, sulfated tin oxide, cerium sulfate on a zirconia support, and vanadium sulfate on a zirconia support, and the solid super base selected from a group consisting of calcium fluoride on a zirconia support, barium fluoride on a zirconia support; potassium-doped magnesium oxide (K-doped/MgO); and sodium oxide on a magnesium oxide support.

3. The process of claim 1, wherein the feedstream also contacts a second catalyst that oxidatively halogenates at least a portion of the methane to yield a mixture comprising at least two members of a group consisting of methyl halide, methylene halide, trihalomethane, carbon tetrahalide, water, hydrogen halide, unreacted halogen, and unreacted oxygen.

4. The process of claim 3, wherein the second catalyst is selected from a group consisting of rare earth halides and rare earth oxyhalides.

5. The process of claim 3, wherein the feedstream contacts the second catalyst before it contacts the first catalyst, contact with the second catalyst yielding the mixture of at least two members of a group consisting of methyl halide, methylene halide, trihalomethane, carbon tetrahalide, water, hydrogen halide, unreacted halogen, and unreacted oxygen, and contact with the first catalyst converting at least a portion of the methylene halide, trihalomethane and carbon tetrahalide to carbon monoxide, hydrogen halide and water.

6. The process of claim 1, wherein the conditions are sufficient to produce an equimolar mixture of carbon monoxide and methyl chloride.

7. The process of claim 1, wherein the feed stream further comprises an amount of carbon monoxide sufficient to provide an equimolar mixture of carbon monoxide and methyl chloride.

8. The process of claim 6, wherein the equimolar mixture of carbon monoxide and methyl chloride contacts a carbonylation catalyst under conditions sufficient to convert at least a portion of the equimolar mixture to at least one of acetyl chloride and acetic acid.

9. The process of claim 1, wherein: a) selectivity to methyl halide falls within a range of from 35 mole percent to 100 mole percent; b) conversion of methane to methyl halide falls within a range of from 0.1 mole percent to 100 mole percent, based upon moles of methane present prior to conversion; c) selectivity to a combination of methyl halide and carbon monoxide falls within a range of from 50 mole percent to 100 mole percent; d) selectivity to methyl halide, relative to selectivity to a combination of methyl halide, methylene halide, trihalomethane and carbon tetrahalide falls within a range of from 85 mole percent to 100 mole percent; or e) a combination of two or more of a) through d) occurs.

* * * * *